US010238729B2

United States Patent
Ioannides

(10) Patent No.: US 10,238,729 B2
(45) Date of Patent: Mar. 26, 2019

(54) CANCER AND SKIN LESION TREATMENT

(71) Applicant: Tim Ioannides, Vero Beach, FL (US)

(72) Inventor: Tim Ioannides, Vero Beach, FL (US)

(73) Assignee: HPVVAX, LLC, Port St. Lucie, FL (US)

( * ) Notice: Subject to any disclaimer, the term of this patent is extended or adjusted under 35 U.S.C. 154(b) by 324 days.

(21) Appl. No.: 14/921,648

(22) Filed: Oct. 23, 2015

(65) Prior Publication Data
US 2016/0114023 A1   Apr. 28, 2016

Related U.S. Application Data

(60) Provisional application No. 62/068,332, filed on Oct. 24, 2014.

(51) Int. Cl.
| | |
|---|---|
| A61K 39/00 | (2006.01) |
| A61K 48/00 | (2006.01) |
| C12N 15/11 | (2006.01) |
| A61K 38/00 | (2006.01) |
| A61K 39/39 | (2006.01) |
| A61K 39/12 | (2006.01) |
| C12N 7/00 | (2006.01) |

(52) U.S. Cl.
CPC .............. *A61K 39/12* (2013.01); *C12N 7/00* (2013.01); *A61K 2039/545* (2013.01); *C12N 2710/20034* (2013.01); *C12N 2710/20071* (2013.01)

(58) Field of Classification Search
CPC ........ A61K 2300/00; A61K 2039/5256; C07K 14/005; C12N 15/86; C12N 2770/36122
See application file for complete search history.

(56) References Cited

U.S. PATENT DOCUMENTS

| | | | |
|---|---|---|---|
| 8,399,610 | B2 | 3/2013 | Man et al. |
| 2005/0287161 | A1 | 12/2005 | Dubin et al. |
| 2007/0218074 | A1 | 9/2007 | Man |
| 2010/0189744 | A1 | 7/2010 | Bryan et al. |
| 2011/0070252 | A1 | 3/2011 | Strome et al. |
| 2011/0110979 | A1 | 5/2011 | Nardelli |
| 2012/0087937 | A1 | 4/2012 | Colau et al. |
| 2012/0100169 | A1 | 4/2012 | Kim et al. |
| 2012/0288538 | A1 | 11/2012 | De Prat Gay et al. |
| 2014/0323437 | A1 | 10/2014 | Hlavinka et al. |
| 2015/0110824 | A1 | 4/2015 | Colau et al. |
| 2015/0299197 | A1 | 10/2015 | Tao et al. |

FOREIGN PATENT DOCUMENTS

| | | |
|---|---|---|
| CN | 101890160 B | 6/2014 |
| WO | WO 20015/054678 A2 | 4/2015 |

OTHER PUBLICATIONS

Venugopal et al., "Recalcitrant cutaneous warts treated with recombinant quadrivalent human papillomavirus vaccine (Types 6, 11, 16 and 18) in a developmentally delayed, 31-year-old white man", Arch Dermatol., 2010, 146(5):475-477.*
Villa et al., "High sustained efficacy of a prophylactic quadrivalent human papillomavirus types 6/11/16/18 L1 virus-like particle vaccine through 5 years of follow-up", British Journal of Cancer, 2006, 95:1459-1466.*
International Search Report (ISR) in PCT/US2017/019433 (copy attached).
Devaraj, KI; Gillison, ML, and WU, TC, Development of HPV vaccines for HPV-associated head and neck squamous cell carcinoma, Crit Rev Oral Biol Med. 2003;14(5):345-62.
International Search Report (ISR) and Written Opinion in PCT/US2015/057150 (corresponding international application.
Villa, L.L, et al., High sustained efficacy of a prophylactic quadrivalent human papilloma virus types 6/11/16/18 L1 virus-ike particle vaccine through 5 years of follow-up, British J. of Cancer (2006) 95, pp. 1459-1466.
Venugopal, S.S. and Murrell, D. F., Recalcitrant Cutaneous Warts Treated with Recombinant Quadrivalent Human Papillomavirus Vaccine (Types 6, 11, 16, and 18) in a Developmentally Delayed, 31-Year-Old White Man, Arch. Dermatol (2010) vol. 146, No. 5 pp. 475-477.
Extended European Search Report. dated Feb. 22, 2018.
Daniel, B., Complete resolution of chronic multiple verruca vulgaris treated with quadirvalent human papilloma virs (HPV) vaccine, J. Am. Acad. Dermatol. Lim, H. (Ed.) AB110, p. 2511, Feb. 2011.
Landis, M., "Recalcitrant plantar warts treated with recombinant quadrivalent human papilloma virus vaccine," Case Letters, J. Am. Acad. Dermatol. Lim, H. (Ed.), pp. e73-e74, Aug. 2012.
Liu, T-Y., et al., "Advances in Peptide-based Human Papillomavirus Therapeutic Vaccines" Current Topics in Medicinal Chemistry, 2012, 12, 1581-1592.

* cited by examiner

Primary Examiner — Barry A Chestnut
(74) Attorney, Agent, or Firm — Ted Whitlock; Lathrop Gage LLP; Allan Sternstein

(57) ABSTRACT

A method for treating or reducing the incidence of recurrence of cancer, benign tumors or HPV-associated lesions, including skin cancer, and particularly squamous cell carcinoma (SCC and basal-cell carcinoma, by administering one or more doses of HPV recombinant vaccine to a patient.

75 Claims, No Drawings

CANCER AND SKIN LESION TREATMENT

CROSS-REFERENCE TO RELATED APPLICATIONS

This is a non-provisional application claiming the benefit of U.S. Provisional Patent Application, Ser. No. 62/068,332, filed Oct. 24, 2014.

BACKGROUND OF THE INVENTION

The invention relates to treating cancer or benign tumors and, more particularly, to a method for treatment, or reducing the incidence of recurrence, of skin cancer or tumors comprising administration of a vaccine, including local administration of the vaccine as a therapeutic agent.

Skin cancer consists of three main types, namely, basal-cell carcinoma (BCC), squamous cell carcinoma (SCC) and melanoma, and is the most common form of cancer globally. Understandably, there have been ongoing studies for many years searching for effective methods to treat, and possibly cure, these types of skin cancer.

It is generally accepted that human papillomavirus (HPV) is associated with causing certain types of skin cancer, particularly squamous cell carcinoma (SCC). HPV is a DNA virus that can infect certain types of tissues in humans. There are upwards of thirty subtypes of HPV and some of these subtypes have been associated with cervical cancer, including HPV16 and HPV18. HPV is not known to be a cause or to be associated with basal cell carcinoma (BCC) or melanoma.

Vaccines have been developed and shown to prevent cervical cancer in women and other conditions caused by or associated with HPV infection. GARDASIL® is a commercially available vaccine having activity against HPV (types 6, 11, 16, and 18).

GARDASIL® 9 is another commercially available vaccine marketed for prevention of HPV (types 16, 18, 31, 33, 45, 52, and 58). GARDASIL® is indicated for use in girls and boys from ages 9-26; GARDASIL® 9 is also indicated for use in girls from ages 9-26, and in boys from ages 9-15.

Other vaccines have been produced, as well, for treating subtypes of HPV, particularly HPV16 and HPV18. GARDASIL® and other known vaccines administered prophylactically, to prevent certain HPV infections and associated cancers, are referred to herein as "preventive vaccines." These preventive vaccines are typically administered for systemic action, being injected into a patient subcutaneously or intramuscularly (e.g., deltoid), remote from any particular target, such as the cervix. Moreover, they are generally accepted to be effective prior to exposure to HPV and are not commonly known to be effective for treatment after exposure to, or infection with, HPV.

Other preventive vaccines include, for example, an improved vaccine composition as described in Chinese Pat App. No. 101890160 (CN '160) comprising certain L1 proteins of HPV (as in GARDASIL®), and additional HPV-specific components. Preventive vaccines comprising HPV-type 16 and 18 proteins are also suggested to provide cross-protection against other HPV types, as described in US Pub. No. 2005/0287161.

Vaccines used for treatment (referred to herein as "therapeutic vaccines") are described. However, these therapeutic vaccines require more than viral-specific components, such as HPV L1 proteins that comprise the commercially available preventive vaccines, such as GARDASIL®.

US Pub. No. 2007/0218074 describes the use of a vaccine composition comprising host-cell peptides from an HPV-infected cell. The host-cell peptides, e.g., the early antigens, E6 or E7, that present on the surface of cells infected with HPV, are fragments of host-cell proteins. The criticality of the polypeptides E6 or E7 in a vaccine used in treating certain cancer types is described in *Development of HPV vaccines for HPV-associated head and neck squamous cell Carcinoma*, Devaraj, et al., Crit Rev Oral Biol Med. 2003; 14(5):345-62. Another vaccine which includes a host-cell protein (BAX) is described in U.S. Pat. No. 8,399,610.

Yet another vaccine composition comprising other or additional antigens in combination with HPV-16 peptides, is a vaccine composition described in US Pub. No. 2011/0070252 which additionally requires Trojan antigen.

US Pub. No. 2011/0110979 (U.S. '979) and US Pub. No. 2012/0288538 (U.S. '538) disclose therapeutic use of an HPV vaccine comprising E6 or E7 polypeptides (peptide fragments from host cells infected with HPV). U.S. '538 describes that E6 and E7 are crucial to induce transformation into HPV-infected cells, and states that a vaccine composition which does not include E6 or E7 would not be expected to work on cells that do not have E6 or E7, i.e., cells such as BCC that are not infected with HPV. The method described in the U.S. '979 publication additionally requires an immunostimulant or adjuvant.

Although the U.S. '979 and U.S. '538 publications describe the use of therapeutic vaccines against skin cancers, such as SCC or epithelial SCC, they do not describe use of the vaccine against other skin cancers, such as BCC or melanoma, likely based on the understanding that BCC and melanoma are not associated with HPV infection.

To the knowledge of the inventor, administration of HPV vaccines comprising only HPV antigens (being free of host-cell peptides), to a previously unimmunized patient, or an adult patient aged 27 or greater, to eliminate or reduce the incidence of recurrence of cancer, benign tumor or other skin lesion, has not been previously described. Nor has the direct or local injection of a vaccine to eliminate the lesion and reduce the incidence of its recurrence been previously described.

The limitations and disadvantages of the above uses of vaccines can be overcome by the use of a method in accordance with the subject invention. There is a need in the medical and health fields for safe and efficacious skin cancer treatments which are convenient for the patient as well as the health practitioner.

SUMMARY OF THE INVENTION

The subject invention concerns a method for treating a patient having cancer, benign tumor, or a human papilloma virus-related (HPV-related) lesion, said method comprising the steps of:

a) administering to a patient 27 years of age or older or a patient previously not immunized with an HPV vaccine, a first dose of an HPV vaccine which is free of host-cell peptide, polypeptide, or protein or a degradant product thereof;

b) administering to the patient a second dose of the HPV vaccine about one month to about three months after the first administration; and c) administering to the patient a third dose of the HPV vaccine about five months to about seven months after the first dose.

In one embodiment, the second dose of HPV vaccine is administered about two months after administering the first dose and the third dose of HPV vaccine is administered about six months after administering the first dose.

The HPV vaccine can be selected from HPV quadrivalent (types 6, 11, 16, and 18) recombinant vaccine comprising HPV L1 proteins and HPV multivalent (types 16, 18, 31, 33, 45, 52, and 58) recombinant vaccine comprising HPV L1 proteins, and preferably is free or substantially free of host-cell early antigen, e.g., E6 or E7.

In one preferred embodiment, the method does not comprise or is without administering an additional or other immunostimulant or adjuvant.

By carrying out the method, the size of the cancer or HPV-related lesion can be substantially reduced, or completely eliminated. In addition, the incidence of recurrence of the cancer or HPV-related lesion can be reduced. The method can be effective in treating or reducing the incidence of recurrence of a cancer, benign tumor, or HPV-related lesion such as squamous cell carcinoma, basal cell carcinoma, melanoma, verruca vulgaris, or condyloma accuminata.

Each dose of HPV vaccine administered in the above method steps is preferably 0.5 ml.

The method can further comprise establishing a positive diagnosis of cancer, benign tumor, or HPV infection prior to administering the first dose of HPV vaccine.

An alternative embodiment of the method according to the subject invention comprises treating a patient having cancer, benign tumor, or a human papilloma virus-related (HPV-related) lesion, wherein the method comprises administering a dose of an HPV vaccine directly to the cancer, tumor, or lesion or an area immediately surrounding the tumor or lesion.

This alternative embodiment of the method according to the subject invention can further comprise the steps of:

administering a second dose of the HPV vaccine directly to the tumor or lesion or an area immediately surrounding the tumor or lesion about one month to about three months after administering the first dose; and optionally, administering a third dose of the HPV vaccine directly to the tumor or lesion or an area immediately surrounding the tumor or lesion about five months to about seven months after administering the first dose.

In this alternative embodiment of the subject method, the second dose of HPV vaccine can be administered about two months after administering the first dose and the third dose of HPV vaccine can be administered about six months after administering the first dose.

By carrying out the alternative embodiment of the method according to the subject invention, the size of the cancer, tumor, or HPV-related lesion can be substantially reduced or completely eliminated. In addition, the incidence of recurrence of the cancer, tumor, or HPV-related lesion can reduced.

The preferred dose of each administration of HPV vaccine, if any, is 0.5 ml.

The method according to any embodiment of the invention can be used for treating cancer, benign tumor, or HPV-related lesion, including, but not limited to, a benign tumor associated or unassociated with HPV infection, squamous cell carcinoma, basal cell carcinoma, melanoma, verruca vulgaris, and condyloma accuminata.

The method can further comprise establishing a positive diagnosis of cancer, benign tumor, or HPV infection prior to administering the first dose of HPV vaccine.

Preferably, the direct or local administration of the vaccine is administered by injection, and more preferably the method does not comprise administering an additional or other immunostimulant or adjuvant, with, during or following the administration of the vaccine.

DETAILED DESCRIPTION

The present invention is directed to a method of treating cancer, benign tumor, and particularly skin cancer, such as squamous cell carcinoma (SCC), or a skin lesion associated with human papilloma virus (HPV) infection. One embodiment of a method according to the subject invention comprises the administration of an HPV vaccine, such as an HPV quadrivalent (types 6, 11, 16, and 18) recombinant vaccine, to a patient that has not been previously immunized with an HPV vaccine, or to an adult patient aged 27 or older. For purposes of the subject invention, a patient previously not immunized with an HPV vaccine is termed an "unimmunized patient" regardless of other immunizations the patient may have received against other conditions or diseases.

The dosing regimen can be in accordance with the conventionally accepted dosing series for a vaccine. For example, HPV vaccines are typically administered using a dosing regimen comprising a first dose, a second dose about two months following the first dose, and a third dose about six months following the first dose.

The method embodiments of the present invention have surprisingly been found to have beneficial results in treating, or minimizing the occurrence, recurrence, and/or progression of, cancer lesions or benign tumors that are not associated with HPV infection, such as basal-cell carcinoma (BBC) or melanoma.

While not being limited to any particular theory, it is proposed that the subject method can increase, i.e. boost a patient's immune response that may manifest clinically as increased surveillance in skin cells to decrease the likelihood of development and progression of abnormal skin cells that produce the skin cancer, particularly, but not exclusively, SCC.

Alternatively, the method of the invention can interfere with inherent functional activities of viral and virus-like proteins by other mechanisms. This interference would include the complete or partial functional inactivation of viral and virus-like materials altered or activated by exogenous and/or environmental agents such as ultraviolet light.

In one embodiment, the HPV vaccine employed in the subject method contains purified inactive viral or virus-like proteins, such as the commercially available GARDASIL®, which is an HPV quadrivalent (types 6, 11, 16, and 18) recombinant vaccine or GARDASIL® 9, an HPV multivalent (types 16, 18, 31, 33, 45, 52, and 58) recombinant vaccine. A vaccine useful in accordance with this embodiment of the subject method is preferably free of host-cell peptide, polypeptide, or protein, such as the early antigens, E6 or E7, which are fragments of host-cell peptides that present on the surface of an HPV-infected cell.

The vaccine can be administered for treating cancerous or benign tumors, including cancer lesions not associated with HPV infection, cancer (tumors or lesions) associated with HPV infection, benign tumors not associated with HPV infection, or non-cancerous HPV-related lesions in an unimmunized patient.

Alternatively, the vaccine can be administered to reduce the incidence of recurrence of cancer, a benign tumor, or an HPV-related lesion in an unimmunized patient. In another embodiment, the vaccine can be administered to treat cancer, benign tumor, or an HPV-related lesion, or reduce the incidence of recurrence thereof, in an adult patient aged 27 or greater.

More particularly, one preferred embodiment of the invention comprises a method for the treatment of cancer, benign tumor or HPV-related lesion, in a patient that is unimmunized, or an adult patient aged 27 or older, comprising the steps of:
  i. administering to the patient a first dose of an HPV recombinant vaccine free of host-cell peptides, polypeptides or proteins;
  ii. administering to the patient a second dose of the HPV recombinant vaccine free of host-cell peptides, polypeptides or proteins between about one month and about three months after the first dose; and
  iii. administering to the patient a third dose of the HPV vaccine free of host-cell peptides, polypeptides or proteins between about five months to about seven months after administering the first dose.

It would be understood by medical practitioners that the reference to the timing of subsequent administrations of the vaccine is approximate and can vary by days or even weeks. This variation can result from patient compliance or non-compliance to the scheduled dosing, clinical observation by the treating physician who may decide to advance (for more aggressive treatment) or delay a subsequent administration for medical reasons. Generally, however, an effective result can be achieved by following a dosing schedule where the second dose is administered about two months following the first dose, and a third dose at about six months after the first dose. Additional (fourth, or fifth) doses can be administered if the physician deems that subsequent administrations can provide benefit to the patient.

A typical total dose for each administration according to the method of the subject invention is about 0.5 ml of the vaccine.

The above method of treatment can be efficacious for treating skin cancer in the patient, and particularly squamous cell carcinoma, wherein a skin cancer lesion is reduced in size or eliminated following the three administrations of the vaccine.

The treatment method according to the subject invention can also reduce the incidence of recurrence of benign tumors or cancer tumors or lesions, including skin cancer, in the patient.

The method can also be effective to reduce the size or eliminate an HPV-associated, but non-cancerous, lesion, such as warts, including genital warts, e.g., verruca vulgaris or condyloma accuminata It is a further unexpected result of the present invention to provide a method of reducing the incidence of recurrence of skin cancer, and particularly squamous cell carcinoma following administration of one or more injections of HPV quadrivalent (types 6, 11, 16, and 18) recombinant vaccine, wherein the vaccine is substantially free of host-cell peptides, polypeptides, or proteins which, as a result of HPV infection of the cell, present on the surface of the infected cell.

Further unexpected results of the subject method of treatment comprise reducing the size of, eliminating, or reducing the incidence of recurrence of skin lesions that are not associated with HPV infection, such as basal cell carcinoma or melanoma.

In one embodiment of the subject invention, the method is carried out without the administration of an additional or other immunostimulant or adjuvant either with, during, or following the treatment method of the invention.

Another embodiment in accordance with the subject invention comprises administering an HPV vaccine administered to a patient by direct or local administration, e.g., injection, into a skin lesion or surrounding area of the lesion. This direct administration method can be useful in patients suffering from cancer, particularly skin cancer. This embodiment of the method can also be useful for treating non-cancerous (benign) tumors, or non-cancerous lesions associated with HPV, such as warts, e.g., verruca vulgaris or condyloma accuminata.

In an embodiment comprising direct injection into or surrounding a lesion, the dosing regimen can comprise a single administration or more than one administration. For example, a three-administration dosing series, as above, can be followed. Alternatively, a physician can administer a subsequent dose as needed (prn) following an initial dose directly into or surrounding the lesion. Divided dosing of the vaccine for any particular single time point is considered to be a single administration.

This direct-administration embodiment of the invention can have beneficial results in treating, or minimizing the occurrence, recurrence, and/or progression of, cancer lesions or tumors such as basal-cell carcinoma (BBC) or melanoma, or non-cancerous (benign) tumors that are not associated with HPV infection.

Any effective HPV vaccine can be employed for administration directly to a cancer or HPV-related lesion. For example, this embodiment of the subject method can comprise direct administering into or surrounding a lesion a vaccine comprising purified inactive viral or virus-like proteins, such as the commercially available GARDASIL®, which is an HPV quadrivalent (types 6, 11, 16, and 18) recombinant vaccine or GARDASIL® 9, an HPV multivalent (types 16, 18, 31, 33, 45, 52, and 58) recombinant vaccine.

A vaccine useful in accordance with this embodiment of the subject method can include host-cell peptides, polypeptides, or proteins, such as the early antigens, E6 or E7 or exclude or be free of host-cell peptides, polypeptides, or proteins, such as the early antigens, E6 or E7. The vaccine can be administered for treating cancer, a benign tumor, or HPV-related lesion in a patient of any age, whether an unimmunized patient or a patient previously immunized with an HPV vaccine.

The vaccine can be directly or locally administered into or surrounding a lesion or tumor to reduce the incidence of recurrence of cancer, benign tumor, or an HPV-related lesion in a patient.

In another embodiment, the vaccine can be administered to treat cancer, benign tumor, or an HPV-related lesion, or reduce the incidence of recurrence thereof, in a patient up to 26 years old or, alternatively, an adult patient aged 27 or greater.

More particularly, one preferred embodiment of the invention comprises a method for the treatment of cancerous or non-cancerous tumor or lesion in a patient comprising the step of administering to the patient a dose of an HPV recombinant vaccine directly to the lesion, tumor, or non-cancerous HPV-related lesion.

Alternatively, the method can comprise the following optional steps:
  i. administering directly to a cancer lesion, benign tumor, or non-cancerous HPV-related lesion of a patient a second dose of the HPV vaccine between about one month and about three months after the first dose; and
  ii. administering directly to a cancer lesion, benign tumor, or non-cancerous HPV-related lesion of a patient a second dose of the HPV vaccine between about five months to about seven months after administering the first dose.

It would be understood by medical practitioners that the reference to the timing of subsequent administrations of the vaccine is approximate and can vary by days or even weeks. This variation can result from patient compliance or non-compliance to the scheduled dosing, clinical observation by the treating physician who may decide to advance (for more aggressive treatment) or delay a subsequent administration for medical reasons. Generally, however, an effective result can be achieved by following a dosing schedule where the second dose is administered about two months following the first dose, and a third dose at about six months after the first dose. Additional (fourth, or fifth) doses can be administered if the physician deems that subsequent administrations can provide benefit to the patient.

A typical total dose for each direct or local administration according to the method of the subject invention is about 0.5 ml of the vaccine. Each 0.5 ml dose can be administered, e.g., by intralesional injection, as a bolus of the entire 0.5 ml or can be administered as a divided dose as a plurality of 0.1-0.2 ml partial administrations into the lesion, an area surrounding the lesion, or both.

The above direct or local administration method of treatment can be efficacious for treating skin cancer in the patient, and particularly squamous cell carcinoma, wherein a skin cancer lesion is reduced in size or eliminated following the three administrations of the vaccine.

The direct or local administration treatment method according to the subject invention can also reduce the incidence of recurrence of cancer, including skin cancer, in the patient.

The direct or local administration method can also be effective to reduce the size or eliminate a benign tumor, whether or not associated with HPV infection, or an HPV-associated, but non-cancerous, lesion, such as warts, including genital warts, e.g., verruca vulgaris or condyloma accuminata.

The direct or local administration method can also be effective to reduce the incidence of recurrence of a benign tumor, whether or not associated with HPV infection, or an HPV-associated, but non-cancerous, lesion, such as warts, including genital warts, e.g., verruca vulgaris or condyloma accuminata It is a further unexpected result of the present invention to provide a method of eliminating or reducing the size or incidence of recurrence of skin cancer, and particularly squamous cell carcinoma following direct or local administration of one or more injections of HPV quadrivalent (types 6, 11, 16, and 18) recombinant vaccine or an HPV multivalent (types 16, 18, 31, 33, 45, 52, and 58) recombinant vaccine.

Further unexpected results of the subject direct or local administration method of treatment comprise reducing the size of, eliminating, or reducing the incidence of recurrence of skin lesions that are not associated with HPV infection, such as basal cell carcinoma or melanoma.

In one embodiment of the subject invention, the direct or local administration method is carried out without the administration of an additional or other immunostimulant or adjuvant.

It is therefore an object of the subject invention to provide a cost-effective, safe, efficacious, and convenient treatment for reducing or ameliorating the growth or size of a cancer tumor or lesion, including a skin cancer lesion such as SCC, BCC or melanoma tumor or lesion. It is another object of the subject invention to provide a cost-effective, efficacious and convenient treatment for curing skin cancer lesions, and yet another object of the invention to provide a cost-effective, efficacious and convenient method to reduce the incidence of recurrence of cancer, including skin cancer lesions.

The subject method of treating or reducing the incidence of recurrence of skin cancer comprises administering an HPV vaccine in one or more doses to a patient. In one embodiment, the method includes administration of a first dose of HPV quadrivalent (types 6, 11, 16, and 18) recombinant vaccine to a patient, a second dose of HPV quadrivalent (types 6, 11, 16, and 18) recombinant vaccine approximately two months thereafter, and a third dose of HPV quadrivalent (types 6, 11, 16, and 18) recombinant vaccine approximately four months after the second dose. In a preferred embodiment, each dose is 0.5 ml.

The subject method can be advantageous in that it can be performed using a commercially available HPV quadrivalent (types 6, 11, 16, and 18) vaccine or HPV multivalent (types 16, 18, 31, 33, 45, 52, and 58) recombinant vaccine as a therapeutic agent rather than or in addition to its use as a preventive vaccine.

A preventive vaccine is understood to be a vaccine composition administered prior to exposure to or infection with an agent such as human papilloma virus (HPV). Preventive vaccines for protection against or prevention of HPV infection and associated cancers are commercially available are therefore known to be safe. GARDASIL® is an HPV quadrivalent (types 6, 11, 16, and 18) recombinant vaccine and GARDASIL® 9, is an HPV multivalent (types 16, 18, 31, 33, 45, 52, and 58) recombinant vaccine currently marketed as a preventive vaccine in the United States by Merck & Co., Inc. Whitehouse Station, N.J. 08889 USA.

By use of a commercially available vaccine, the vaccine can be readily accessed by a physician or healthcare practitioner. Moreover, the use of an HPV quadrivalent (types 6, 11, 16, and 18) recombinant vaccine or HPV multivalent (types 16, 18, 31, 33, 45, 52, and 58) recombinant vaccine in accordance with the subject method do not require secondary or additional immunostimulants or adjuvants. These commercially available HPV quadrivalent (types 6, 11, 16, and 18) or HPV multivalent (types 16, 18, 31, 33, 45, 52, and 58) recombinant vaccines are free, or substantially free, of host-cell peptides, polypeptides, or proteins, such as the antigens, E6 or E7.

Advantageously, the unexpected result of treating cancer, benign tumor, or HPV-related skin lesions, including skin cancers that are associated with HPV infection or skin cancers that are not associated with HPV infection, can be achieved using the subject method as described herein.

The following charts provide the results from the subject method of treatment carried out in three patients experiencing relatively frequent recurrence rates of skin cancer, including squamous cell carcinoma (SCC) as well as basal-cell carcinoma.

The data presented below represents an average number of distinctive recurrences of skin cancer per month for a period of time prior to and after undergoing the method of treatment described herein.

Example 1—Patient 1

Patient 1 was administered three 0.5 ml doses, including a first 0.5 ml dose, a second 0.5 ml dose two months later, and a third 0.5 ml dose four months after the second dose. In a follow-up exam three months after administration of the third dose of HPV quadrivalent (types 6, 11, 16, and 18) recombinant vaccine, Patient 1 had experienced zero recurrences of skin cancer, including both SCC and BCC types, during the three month period. Prior to commencement of the treatment method, Patient 1 had more than 300 distinctive occurrences of skin cancer during his lifetime.

| PATIENT 1 | | | |
|---|---|---|---|
| | Time Period (Months) | SCC | BCC |
| Prior to Commencement of Treatment Method | 16 | 1.80 | 0.25 |
| After Commencement of Treatment Method | 16 | 0.37 | 0.00 |

Example 2—Patient 2

Patient 2 was administered three 0.5 ml doses of HPV quadrivalent (types 6, 11, 16, and 18) recombinant vaccine, including a first 0.5 ml dose, a second 0.5 ml dose two months later, and a third 0.5 ml dose four months after the second dose.

| PATIENT 2 | | | |
|---|---|---|---|
| | Time Period (Months) | SCC | BCC |
| Prior to Commencement of Treatment Method | 13 | 2.07 | 0.53 |
| After Commencement of Treatment Method | 13 | 0.23 | 0.3 |

Example 3—Patient 3

Patient 3 was administered three 0.5 ml doses of HPV quadrivalent (types 6, 11, 16, and 18) recombinant vaccine, including a first 0.5 ml dose, a second 0.5 ml dose two months later, and a third 0.5 ml dose eight months after the second dose.

| PATIENT 3 | | | |
|---|---|---|---|
| | Time Period (Months) | SCC | BCC |
| Prior to Commencement of Treatment Method | 22 | 0.18 | 0.13 |
| After Commencement of Treatment Method | 22 | 0.09 | 0.04 |

As a group, each of the patients who underwent the method of treatment using HPV quadrivalent (types 6, 11, 16, and 18) recombinant vaccine experienced a significant decrease in the number of skin cancer recurrences, as well as improvement in the texture and appearance of the skin with decreased scaling and an increase in general skin suppleness.

Generally, the method of treatment described herein serves to effectively increase, i.e. boost, the patient's immune surveillance in skin cells in order to decrease the likelihood of a development of abnormal skin cells that produce the skin cancer. The method of the present invention has been shown to treat and prevent recurrence of SCC, and to significantly reduce recurrence of BCC. It is also possible that the increase in immune surveillance, as a result of the treatment method, will concomitantly decrease the incidence of malignant melanoma.

In one embodiment, the method of treatment for eliminating or reducing the incidence of recurrence of skin cancer includes administering the HPV quadrivalent (types 6, 11, 16, and 18) recombinant vaccine in the form of an injection directly into the cancerous tissue or an area of tissue immediately surrounding the cancerous tissue.

Use of other HPV vaccines is fully contemplated within the scope of the invention.

While the present invention has been presented in accordance with several preferred and practical embodiments thereof, it is recognized that departures from the instant disclosure are fully contemplated within the spirit and scope of the invention.

What is claimed is:

1. A method for treating a patient having cancer, said method comprising the steps of:
    a) administering to a patient 27 years of age or older or a patient previously not immunized with an HPV vaccine, a first dose of an HPV vaccine which is free of host-cell peptide, polypeptide, or protein or a degradant product thereof;
    b) administering to the patient a second dose of the HPV vaccine about one month to about three months after the first administration; and
    c) administering to the patient a third dose of the HPV vaccine about five months to about seven months after the first dose wherein the cancer is treated.

2. The method of claim 1 wherein the second dose of HPV vaccine is administered about two months after administering the first dose and the third dose of HPV vaccine is administered about six months after administering the first dose.

3. The method of claim 1 wherein the HPV vaccine is selected from the group consisting of HPV quadrivalent (types 6, 11, 16, and 18) recombinant vaccine comprising HPV L1 proteins and HPV multivalent (types 16, 18, 31, 33, 45, 52, and 58) recombinant vaccine comprising HPV L1 proteins.

4. The method of claim 1 wherein the vaccine is substantially free of host-cell early antigen, E6 or E7.

5. The method of claim 1 wherein the method does not comprise or excludes administering an additional or other immunostimulant or adjuvant.

6. The method of claim 1 wherein the size of the cancer is substantially reduced.

7. The method of claim 1 wherein the cancer is eliminated.

8. The method of claim 1 whereby the incidence of recurrence of the cancer is reduced.

9. The method of claim 1 wherein each dose of HPV vaccine is 0.5 ml.

10. The method of claim 1 wherein the cancer is selected from the group consisting of squamous cell carcinoma, basal cell carcinoma, and melanoma.

11. The method of claim 1 wherein the method further comprises:
    establishing a positive diagnosis of cancer, diagnosis of benign tumor, or diagnosis of HPV infection prior to administering the first dose of HPV vaccine.

12. A method for treating a patient having cancer, said method comprising the step of:
    a) administering a dose of an HPV vaccine directly to the cancer or an area immediately surrounding the cancer.

13. The method of claim 12, further comprising the steps of:
    b) administering a second dose of the HPV vaccine directly to the cancer, or an area immediately surrounding the cancer, about one month to about three months after administering the first dose; and c) optionally, administering a third dose of the HPV vaccine directly to the cancer, or an area immediately surrounding the cancer, about five months to about seven months after administering the first dose.

14. The method of claim 13 wherein the second dose of HPV vaccine is administered about two months after administering the first dose and the third dose of HPV vaccine is administered about six months after administering the first dose.

15. The method of claim 12 wherein the cancer is eliminated or substantially reduced in size.

16. The method of claim 12 whereby the incidence of recurrence of the cancer is reduced.

17. The method of claim 12 wherein the dose of HPV vaccine administered is 0.5 ml.

18. The method of claim 12 wherein the cancer is selected from the group consisting of squamous cell carcinoma, basal cell carcinoma, and melanoma.

19. The method of claim 12 wherein the method further comprises:
establishing a positive diagnosis of cancer prior to administering the first dose of HPV vaccine.

20. The method of claim 12 wherein the vaccine is administered by injection.

21. The method of claim 12 wherein the method does not comprise or excludes administering an additional or other immunostimulant or adjuvant.

22. A method for treating a patient having a cancerous tumor said method comprising the steps of:
a) administering to a patient having a cancerous tumor, and being 27 years of age or older or a patient previously not immunized with an HPV vaccine, a first dose of an HPV vaccine comprising at least one viral L1 protein which is free of non-L1 viral peptide, polypeptide, or protein or a degradant product thereof;
b) administering to the patient a second dose of the HPV vaccine about one month to about three months after the first administration; and
c) administering to the patient a third dose of the HPV vaccine about five months to about seven months after the first dose.

23. The method of claim 22 wherein the second dose of HPV vaccine is administered about two months after administering the first dose and the third dose of HPV vaccine is administered about six months after administering the first dose.

24. The method of claim 22 wherein the HPV vaccine is selected from the group consisting of HPV quadrivalent (types 6, 11, 16, and 18) recombinant vaccine comprising HPV L1 proteins and HPV multivalent recombinant vaccine comprising HPV L1 proteins of HPV types 16, 18, 31, 33, 45, 52, and 58.

25. The method of claim 22 wherein the method does not comprise or excludes administering a second composition comprising an immunostimulant or an adjuvant.

26. The method of claim 22 wherein the cancer or HPV-associated lesion is selected from the group consisting of squamous cell carcinoma, basal cell carcinoma, melanoma, verruca vulgaris, and condyloma accuminata.

27. A method for treating a patient having a cancerous tumor, said method comprising the step of:
a) administering a dose of an HPV vaccine to patient with a cancerous tumor, wherein administration is directly into said tumor; and
b) administering a second dose of HPV vaccine about two months after administering the first dose and the third dose of HPV vaccine is administered about six months after administering the first dose.

28. The method of claim 27, further comprising the steps of:
c) administering a second dose of the HPV vaccine directly to the cancerous tumor, about one month to about three months after administering the first dose; and
d) optionally, administering a third dose of the HPV vaccine directly to said cancerous tumor about five months to about seven months after administering the first dose.

29. The method of claim 27 wherein the cancerous tumor is eliminated or substantially reduced in size.

30. The method of claim 27 whereby recurrence of cancer is reduced.

31. The method of claim 27 wherein the cancer is selected from the group consisting of squamous cell carcinoma, basal cell carcinoma, and melanoma.

32. The method of claim 27 wherein the vaccine is administered by injection.

33. The method of claim 27 wherein the method does not comprise or excludes administering a second composition comprising an immunostimulant or adjuvant.

34. The method of claim 1 wherein the cancer is a cancerous tumor.

35. The method of claim 12, wherein the cancer is a cancerous tumor.

36. A method for treating a patient having cancer, said method comprising the step of:
administering to a patient 27 years of age or older or a patient previously not immunized with an HPV vaccine, a first dose of an HPV vaccine which is free of host-cell peptide, polypeptide, or protein or a degradant product thereof,
whereby the cancer is treated.

37. The method of claim 36, said method further comprising the step of:
administering to the patient a second dose of the HPV vaccine about one month to about three months after the first administration.

38. The method of claim 37, said method further comprising the step of:
administering to the patient a third dose of the HPV vaccine about five months to about seven months after the first dose.

39. The method of claim 37 wherein the second dose of HPV vaccine is administered about two months after administering the first dose.

40. The method of claim 38 wherein the third dose of HPV vaccine is administered about six months after administering the first dose.

41. The method of claim 36 wherein the HPV vaccine is selected from the group consisting of HPV quadrivalent (types 6, 11, 16, and 18) recombinant vaccine comprising HPV L1 proteins and HPV multivalent (types 16, 18, 31, 33, 45, 52, and 58) recombinant vaccine comprising HPV L1 proteins.

42. The method of claim 36 wherein the vaccine is substantially free of host-cell early antigen, E6 or E7.

43. The method of claim 36 wherein the method does not comprise or excludes administering an additional or other immunostimulant or adjuvant.

44. The method of claim 36 wherein the HPV vaccine is administered systemically.

45. The method of claim 36 wherein the size of the cancer is substantially reduced.

46. The method of claim 36 wherein the cancer is eliminated.

47. The method of claim 36 whereby the incidence of recurrence of the cancer is reduced.

48. The method of claim 36 wherein the dose of HPV vaccine is 0.5 ml.

49. The method of claim 36 wherein the cancer is selected from the group consisting of squamous cell carcinoma, basal cell carcinoma, and melanoma.

50. The method of claim 1 wherein the cancer is squamous cell carcinoma.

51. The method of claim 1 wherein the cancer is basal cell carcinoma.

52. The method of claim 1 wherein the cancer is melanoma.

53. The method of claim 12 wherein the cancer is squamous cell carcinoma.

54. The method of claim 12 wherein the cancer is basal cell carcinoma.

55. The method of claim 12 wherein the cancer is melanoma.

56. The method of claim 36 wherein the cancer is squamous cell carcinoma.

57. The method of claim 36 wherein the cancer is basal cell carcinoma.

58. The method of claim 36 wherein the cancer is melanoma.

59. The method of claim 36 wherein the cancer is a cancerous tumor.

60. A method for treating a patient having cancer, said method comprising the step of:
   a) systemically administering to a patient 27 years of age or older or a patient previously not immunized with an HPV vaccine, a first dose of an HPV vaccine which is free of host-cell peptide, polypeptide, or protein or a degradant product thereof, and
   b) administering a dose of an HPV vaccine directly to the cancer or an area immediately surrounding the cancer, whereby the cancer is treated.

61. The method of claim 60, said method further comprising the step of:
   c) administering to the patient a second dose of the HPV vaccine systemically and directly to the cancer or area immediately surrounding the cancer about one month to about three months after the first administration.

62. The method of claim 61, said method further comprising the step of:
   d) administering to the patient a third dose of the HPV vaccine systemically and directly to the cancer or area immediately surrounding the cancer about five months to about seven months after the first dose.

63. The method of claim 61 wherein the second dose of HPV vaccine is administered about two months after administering the first dose.

64. The method of claim 62 wherein the third dose of HPV vaccine is administered about six months after administering the first dose.

65. The method of claim 60 wherein the HPV vaccine is selected from the group consisting of HPV quadrivalent (types 6, 11, 16, and 18) recombinant vaccine comprising HPV L1 proteins and HPV multivalent (types 16, 18, 31, 33, 45, 52, and 58) recombinant vaccine comprising HPV L1 proteins.

66. The method of claim 60 wherein the vaccine is substantially free of host-cell early antigen, E6 or E7.

67. The method of claim 60 wherein the method does not comprise or excludes administering an additional or other immunostimulant or adjuvant.

68. The method of claim 60 wherein the size of the cancer is substantially reduced.

69. The method of claim 60 wherein the cancer is eliminated.

70. The method of claim 60 whereby the incidence of recurrence of the cancer is reduced.

71. The method of claim 60 wherein each dose of HPV vaccine is 0.5 ml.

72. The method of claim 60 wherein the cancer is selected from the group consisting of squamous cell carcinoma, basal cell carcinoma, and melanoma.

73. The method of claim 60 wherein the cancer is squamous cell carcinoma.

74. The method of claim 60 wherein the cancer is basal cell carcinoma.

75. The method of claim 60 wherein the cancer is a cancerous tumor.

* * * * *